United States Patent [19]

Alvarado

[11] Patent Number: 4,815,465
[45] Date of Patent: Mar. 28, 1989

[54] DISSECTOR DEVICE

[76] Inventor: Alfredo Alvarado, 4310 Bayview Dr., Ft. Lauderdale, Fla. 33308

[21] Appl. No.: 170,071

[22] Filed: Mar. 14, 1988

Related U.S. Application Data

[63] Continuation of Ser. No. 897,198, Aug. 18, 1986, abandoned.

[51] Int. Cl.$^4$ .............................................. B61B 17/32
[52] U.S. Cl. ................................ 128/305; 128/334 R; 128/329 R
[58] Field of Search ............ 128/305, 305.5, 335, 128/325–326, 334 R, 329 R

[56] References Cited

U.S. PATENT DOCUMENTS

| | | | |
|---|---|---|---|
| 3,584,628 | 6/1971 | Green | 128/305 |
| 3,653,117 | 4/1972 | Wolfberg et al. | 128/334 R |
| 3,735,762 | 5/1973 | Bryan et al. | 128/305 |
| 4,058,126 | 11/1977 | Leveen | 128/305 |
| 4,368,734 | 1/1983 | Banko | 128/305 |
| 4,595,007 | 6/1986 | Mericle | 128/334 R |
| 4,596,249 | 6/1986 | Freda et al. | 128/334 R |

*Primary Examiner*—C. Fred Rosenbaum
*Assistant Examiner*—Gene B. Kartchner
*Attorney, Agent, or Firm*—Oltman and Flynn

[57] ABSTRACT

A dissector device to be incorporated into the anvil-jaw of a ligation and division stapler to facilitate its use. Such device is inserted with ease through a relatively small opening in the neighboring tissues of the blood vessels to be ligated and divided. By using the dissector device the surgical operation is easier, faster and safer than when using the prior art ligation and division stapler.

5 Claims, 2 Drawing Sheets

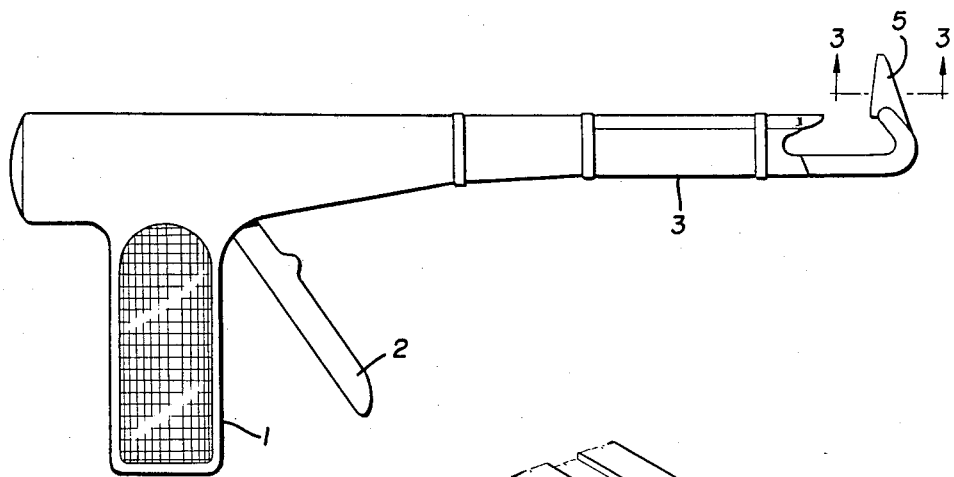
FIG. 3
FIG. 1
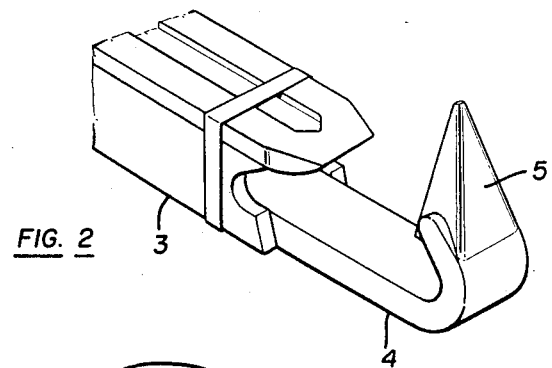
FIG. 2
FIG. 5
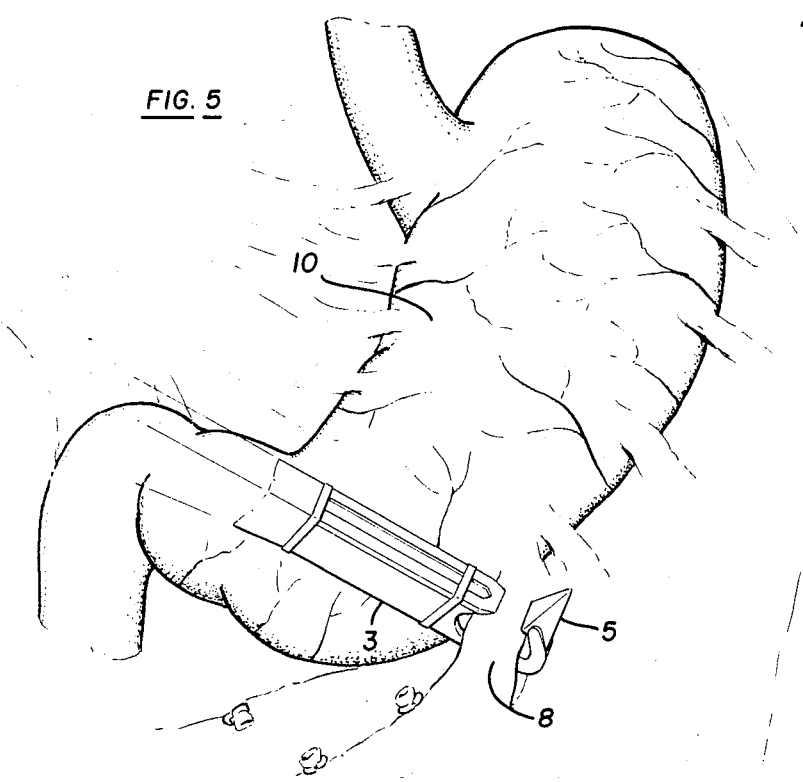

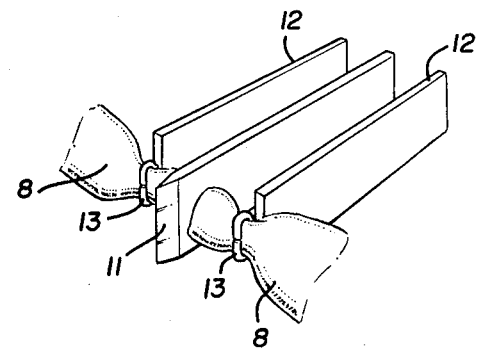
FIG. 6 (PRIOR ART.)
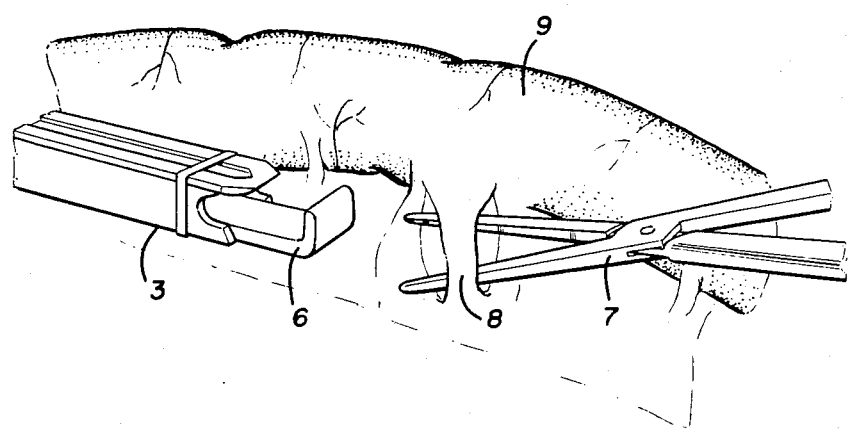
FIG. 4 (PRIOR ART.)

DISSECTOR DEVICE

BACKGROUND OF THE INVENTION

This application is a continuation of application Ser. No. 897,198, filed Aug. 18, 1986, now abandoned.

1. Field of the invention.

This invention relates to the field of surgical staplers particularly to the ligation and division stapler.

2. Description of prior art.

A ligation and division stapler instrument is in use at present to expediently ligate and transect blood vessels in operations of the stomach or intestines. This instrument places two staples around the vessels closing them securely, and simultaneously dividing the vessels with a blade between the staples. In many instances problems are encountered trying to introduce the instrument into the tissues due to the blunt configuration of the anvil-jaw even with the aid of a clamp to feed the tissue into the instrument. Furthermore by trying to introduce such a blunt part of the instrument around the delicate vessels of the aforementioned organs these vessels may be torn apart producing annoying bleeding. Besides this it takes longer to introduce the blunt anvil-jaw of the instrument currently in use because it requires previous dissection of the vessels to be ligated with a dissecting instrument such as a clamp or scissors.

BRIEF DESCRIPTION OF THE INVENTION

The main purpose of this invention is to facilitate the insertion of the anvil-jaw of the instrument into the tissues around the blood vessels to be ligated and divided. Another object of this invention is to prevent injury to these vessels by minimizing the dissection of the tissues around them. It is also the object of the invention to expedite the procedure of ligating and dividing the vessels since the dissecting device is easier to manipulate and therefore saves considerable operative time with obvious advantages to the patient.

BRIEF DESCRIPTION OF THE DRAWINGS

For the purpose of illustrating the invention, there is shown in the drawings a form which is presently preferred; it being understood, however, that this invention is not limited to the precise configuration shown.

FIG. 1 is a perspective view of a ligation and division stapler instrument provided with the anvil-jaw dissector device.

FIG. 2 is a partial perspective view of the lower end of the instrument depicting the anvil-jaw dissector device in more detail.

FIG. 3 is a cross-section of the dissector device taken along the line X—X of FIG. 1.

FIG. 4 shows the current method of introducing the blunt jaw of the instrument into the tissues surrounding the blood vessels to be ligated and divided with the aid of a clamp.

FIG. 5 shows the way in which the dissector device is introduced into the tissues requiring minimal dissection and without the use of a clamp.

FIG. 6 is a fragmentary perspective view showing the knife and staples after being applied to the blood vessels.

DETAILED DESCRIPTION OF THE INVENTION

In all the figures like parts have been given like numerals. Reference is made to FIGS. 1 to 6.

In FIG. 1 a ligation and division stapler instrument having the dissector device is depicted. The instrument is activated by squeezing handles 1 and 2 together as in the prior art instrument. The dissector device 5 has been incorporated to the forward portion of of anvil-jaw 4. The lower portion of the instrument 3 contains the open staples and respective pushers, as well as the dividing knife (not described herein).

In FIG. 2 the lower portion of the instrument 3 is depicted in a perspective view and shows in detail the preferred configuration of the dissector device 5 intimately connected to or forming part of anvil-jaw 4.

FIG. 3 is a front sectional view of the dissector device taken along the line X—X of FIG. 1.

FIG. 4 shows the prior art ligation and division stapler with its blunt anvil-jaw 6 ready to be inserted in the relatively large opening made around the blood vessels 8 by dissection with a clamp. Notice that this opening should be big enough to pass the blunt anvil-jaw without tearing apart the delicate vessels 8 of the small bowel 9.

FIG. 5 shows the ligation and division stapler provided with the dissector device 5 already introduced into the relatively small opening around the blood vessels 8 of the stomach 10 and without benefit of a clamp 7 as in the previous figure. This clearly makes the operation easier, faster and safer than when using the prior art instrument.

FIG. 6 shows the blood vessels 8 being ligated with staples 13 and simultaneously divided by knife 11. The pushers 12 are squeezing the staples to their final configuration around the vessels 8.

I claim:

1. A surgical stapling instrument having an anvil-jaw at a distal end of the instrument, comprising means for ligation and division of blood vessels and means for dissecting the tissues around the vessels, said dissecting means disposed at the distal end of the instrument, said dissecting means including an upstanding substantially pyramid-shaped dissector device intimately connected to and framing part of the anvil-jaw, and, said pyramid-shaped dissector having a base which is substantially quadrilateral and a vertex of the pyramid facing away from said anvil-jaw.

2. Surgical instrument according to claim 1, wherein said vertex is slightly truncated and slightly rounded.

3. Surgical instrument according to claim 1 wherein said dissector device is made of metal.

4. Surgical instrument according to claim 3, wherein said metal is surgical steel.

5. Surgical instrument according to claim 3, wherein said ligation and division means include: two pushers for ligation of said vessels and a dividing knife disposed between said pushers for dividing the vessels, and squeezing handles disposed at the proximal end of the instrument for activatig the instrument.

* * * * *